United States Patent
Hagihara et al.

[11] 4,407,291
[45] Oct. 4, 1983

[54] TRANSCUTANEOUS BLOOD OXYGEN MEASURING DEVICE

[75] Inventors: Bunji Hagihara, 8-17, Fujishirodai 2-chome, Suita, 565; Tamotsu Fukai, Osaka; Kikuo Nomura, Osaka; Kenichi Yoshida, Osaka; Isao Isshiki, Osaka, all of Japan

[73] Assignees: Sumitomo Electric Industries Ltd., Osaka; Bunji Hagihara, Suita, both of Japan; part interest to each

[21] Appl. No.: 176,033

[22] Filed: Aug. 7, 1980

Related U.S. Application Data

[63] Continuation-in-part of Ser. No. 34,132, Apr. 27, 1979, abandoned.

[30] Foreign Application Priority Data

May 12, 1978 [JP] Japan .................... 53-63373[U]

[51] Int. Cl.³ .................................................. A61B 5/00
[52] U.S. Cl. ..................................... 128/635; 204/403; 204/415
[58] Field of Search ............... 128/635; 204/195 B, 204/195 P, 403, 415

[56] References Cited

U.S. PATENT DOCUMENTS

| | | | |
|---|---|---|---|
| 3,795,239 | 3/1974 | Eberhard et al. | 128/635 |
| 3,838,034 | 9/1974 | Groves | 204/195 B |
| 4,185,620 | 1/1980 | Hagihara | 128/635 |

FOREIGN PATENT DOCUMENTS

| | | | |
|---|---|---|---|
| 2276026 | 1/1976 | France | 128/635 |
| 2003275 | 3/1979 | United Kingdom | 128/635 |

OTHER PUBLICATIONS

Jesterager, P. "Meas. of Oxy.", Proceed. of Interdisciplinary Sym. Odense Univ. Denmark, Sep. 26–27, 1974, p. 260–270.
Jesterager, P. Scand. J. Clin. Lab. Invest., 37(Suppl. 146) 1977, pp. 27–30.
Huch, A. et al., Scand. J. Clin. Lab. Invest., 31, 269–275, 1973.
Huch, R. et al., J. Perinat. Med., (1973) 183–191.
Scacci, R. et al., Med. Instr. 10, No. 4, Jul.–Aug. (1976) 192–194.

Primary Examiner—Lee S. Cohen
Attorney, Agent, or Firm—Cushman, Darby & Cushman

[57] ABSTRACT

A transcutaneous blood oxygen measuring device is disclosed for the noninvasive measurement of oxygen partial pressure in arterial blood which includes a cathode surrounded by an anode held together by an insulating plastic in an electrode part, a heating portion to heat the skin of a subject to which the device is applied and to receive the electrodes plus an electrolyte. The heating portion has an opening to indirectly expose the electrodes, via an electrolyte and associated membrane, to the subject's skin surface. Adjacent the working surfaces of each electrode an electrolyte is provided, retained by an oxygen permeable membrane which, in turn, is brought into contact with the subject's skin. The working face of one electrode, typically the cathode, is extended beyond the plane of the working face of the other electrode; the opening in the heater is smoothly rounded and the cathode plus tapered hole, both having approximately the same cross-sectional area, are placed in close proximity with each other.

9 Claims, 3 Drawing Figures

TRANSCUTANEOUS BLOOD OXYGEN MEASURING DEVICE

BACKGROUND OF THE INVENTION

Cross-Reference to Related Applications

This is a continuation-in-part of our earlier application Ser. No. 34,132 filed Apr. 27, 1979, now abandoned.

Field of the Invention

This invention relates to an improved electrode assembly used as a transcutaneous blood oxygen measuring device for measuring the concentration of oxygen in blood, namely the oxygen partial pressure $PO_2$ particularly in arterial blood of a subject.

Prior Art

The measurement of oxygen partial pressure $PO_2$ in blood, especially in arterial blood, is an important matter in breath control of a new-born baby or patient in intensive care.

In the past, for measuring the concentration of oxygen in blood, namely the oxygen partial pressure in a blood, sometimes expressed as $PaO_2$ as arterial oxygen pressure, a method of directly measuring the partial pressure of the blood extracted from an artery has been generally used. However, such method is not suitable for continuous measurements, and moreover, the method causes pain for the patient. Especially for a new-born baby, breath control is necessary in order to prevent impediment of brain or other fatal impediments due to low oxygen concentration on the one hand or to prevent damage to the retina due to excessive oxygen concentration on the other. For such a new-born baby, the oxygen concentration in a controlled atmosphere surrounding the baby must be carefully controlled by using the measured value of oxygen partial pressure in arterial blood, and for that purpose a continuous or real-time measurement of oxygen partial pressure is necessary.

The transcutaneous oxygen electrode method, being different from the direct measurement approach, does not give the patient any pain. The method is suitable for long continuous measurement, since it catches oxygen at the skin surface and measures the oxygen which diffuses from the blood and through the skin. The transcutaneous oxygen electrode method uses a special composite electrode called a Clark element, which comprises a constant-temperature heating means to warm the patient's skin. When it is attached on the patient's skin, oxygen diffusing from the subcutaneous tissue reaches the surface of the cathode of noble metal, such as platinum or gold, through an electrode membrane disposed between the skin and the electrodes. Then the oxygen reacts with the cathode and is reduced to water. By measuring the electrolytic current produced by the chemical reaction, the oxygen partial pressure $PO_2$ can be obtained. In such measurement, by heating the part of the skin that contacts the electrode to a suitable temperature, the subcutaneous tissue is locally arterialized, thereby making the oxygen partial pressure to be measured substantially equal to that of the arterial blood.

The principle of the transcutaneous measurement of the partial oxygen concentration of artery blood oxygen is elucidated as follows. When a sensor having an anode of silver and a cathode of a noble metal, such as platinum or gold, is applied to the skin of a patient using a double-face adhesive tape and the anode is heated to 43° to 44° C., the skin tissue at the part under the anode and its neighboring skin tissue is heated thereby arterializing the skin tissue. As a result the partial oxygen pressure in the blood vessel in the heated skin tissue becomes substantially equal to that in the arterial blood. Oxygen diffuses from the blood vessel through the skin tissue, passes a membrane covering the contacting faces of the electrodes, and dissolves in the electrolyte which is held between the membrane and the electrode faces and reaches the surface of the cathode. The electrolyte consists primarily of a potassium chloride solution. When a D.C. potential of between 0.5 and 0.8 volts is applied across the cathode and the anode in a manner to make the anode positive to the cathode, by reaching of oxygen from the arterial blood to the electrode surfaces, a reduction reaction of the oxygen takes place at the cathode surface when the oxygen from the arterial blood reaches it, and an oxidation reaction of the silver takes place at the anode. That is to say, on the surface of the cathode of gold or platinum, the reduction reaction is, in case that the electrolyte is acidic:

$$O_2 + 4H^+ + 4e \rightarrow 2H_2O \qquad (1),$$

or, in a case where the electrolyte is basic:

$$O_2 + 2H_2O + 4e \rightarrow 4OH^{31} \qquad (2).$$

In both of the above reactions, electrons of a number proportional to the amount of the $O_2$ molecules reaching the cathode are consumed.

At the same time, on the surface of the silver anode, the oxidation reaction is, for any value of pH:

$$4Ag + 4Cl^- \rightarrow 4AgCl + 4e \qquad (3)$$

thus electrons of the number corresponding to the amount of the $O_2$ reaching the cathode are produced. Accordingly, a current flows between the anode and the cathode, and the intensity of the current is proportional to the number of oxygen molecules which pass through the membrane and hence is proportional to the partial oxygen pressure in the subcutaneous tissue and to the arterial blood.

A transcutaneous blood oxygen measuring device shown in FIG. 1 consists of a covering electrode part 1 made of a heat-insulating and electrically insulating plastics material, a receptacle shaped to receive the electrode part, and a disposable membrane part 3 having an oxygen permeable membrane 8 and disposed in a space formed between the electrode part 1 and the heating part 2 and a sealing ring 4 to seal the space between the electrode part 1 and the membrane 8, for retaining electrolyte E. A heater 5 is embedded in a circular hollow provided in a ring-shaped metal block which houses the heating part 2, the heater 5 being connected to lead wires 18. Connecting bolts 6 (only one is shown in this view) connect the electrode part 1 and the heating part 2 with the membrane part 3 positioned inbetween.

The heating part 2 includes a centrally extended plate-shaped skin heating surface 7 having a round opening 14 at its center, and a temperature detecting element 15 such as thermistor which in operation provides a detection signal through lead wires 19 to a known control circuit for controlling the current supplied to heater 5.

In this device the electrode part 1 has a thin tube-shaped cathode 10 made of a noble metal such as platinum or gold, a thick tube-shaped anode 11 made of silver and coaxially disposed to surround the cathode 10 plus an insulator 12 such as glass or epoxy resin filling the spaces in anode 11 and in cathode 10. The lead out wires 16 and 17 are provided for connecting the cathode 10 and anode 11, respectively, to a known electronic circuit.

In the type of construction discussed above, the electrolyte E is present in at least a thin gap between the lower end faces of the cathode 10 and the anode 11 and the insulator 12 and the membrane 8. In this manner, in operation the oxygen coming from the patient's subcutaneous tissue and passing through the oxygen permeable membrane 8 electrochemically reacts with the electrolyte E. Thus by measuring the electrochemical quantity produced in the reaction, oxygen concentration or oxygen partial pressure can be measured.

However in a device of the type described and illustrated in FIG. 1, various precautions and procedures must be taken in order to assure accurate measurements. For instance, the opening 14 should be attached to the subject's skin at a place having the same or corresponding curvature. The device should be attached to the skin with the same contact pressure. Further, the device should be attached to the skin with such a moderate pressure that the skin does not unnecessarily press the membrane as to squeeze out the electrolyte from the thin gap between the lower end faces of the cathode 10 and the anode 11 retained in the insulator 11 and the membrane itself. Insufficient or no electrolyte renders the measurements inaccurate.

Additionally, since a considerable area of the membrane itself is exposed, defined by the size of the opening 14 of the skin heating part 7, it is sometimes difficult to maintain substantially the same temperature between that portion of the skin surface which is directly under the cathode 10 and the temperature of the surrounding skin.

SUMMARY OF THE INVENTION

The present invention provides an improved transcutaneous blood oxygen measuring device capable of more accurate measurement than previous devices. These and other advantages will be apparent from the appended claims and the following detailed description.

DETAILED DESCRIPTION OF THE PREFERRED EMBODIMENTS

Our invention is directed to an improved transcutaneous blood oxygen measuring device including an electrode portion having a cathode and an anode surrounding said cathode, isolated by an insulator or electrode between the two, the electrode part having an end face in which an end part or working face of the cathode is disposed encircled by the working face of the anode. Preferably the two electrode working surfaces are coaxial with each other.

The device has a heater with a skin heating portion and a skin contacting face at the bottom adapted to contact the skin surface of a subject. An opening is formed on said skin contacting face thereby placing the electrodes, via an electrolyte and oxygen permeable membrane, in contact with the subject's skin. The heater also acts as a receptacle into which the electrodes, plus associated structure, are placed and sealed. An oxygen permeable membrane is placed between the heating part and the working faces of each electrode. This serves to cover the end faces and retain a liquid electrolyte in the space between the oxygen permeable membrane and the electrode face.

The device is improved in that the working face of the cathode is extended well beyond that of the anode to protrude into the opening of the hole in the heater. The opening is slightly larger in cross-sectional size than the working face of the cathode. The opening is provided with smooth, rounded shoulders to define a generally correspondingly shaped area between both electrode working faces and the opening.

Using the specific type of construction, we are able to narrowly limit the area of the opening of the plate-shaped skin heating part, and as a consequence the area of the opening exposing the membrane keeps the membrane in tight contact with the skin surface. This structure prevents the electrolyte from being squeezed out of the gap between the electrodes 10, 11 and insulator 12 and the side walls of the skin heating part 7. As a result, the skin surface is maintained at a more uniform temperature in the area exposed through the opening.

Figure 1:
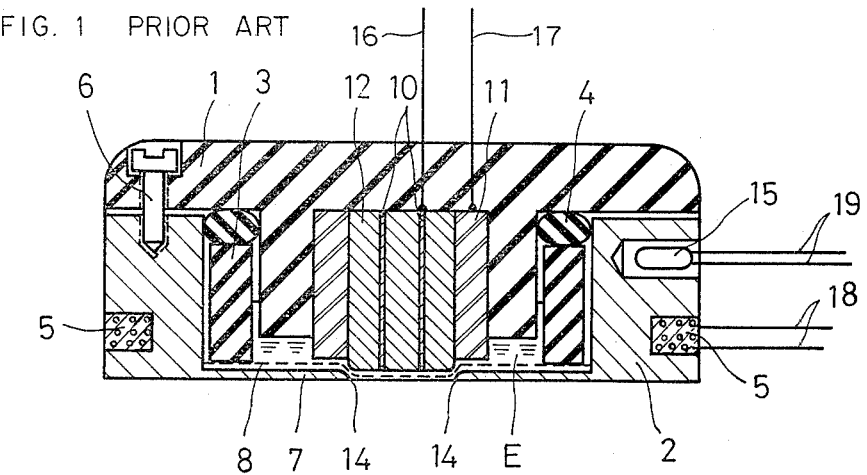
FIG. 1 is a sectional elevation view of a transcutaneous blood oxygen measuring device.
Figure 2:
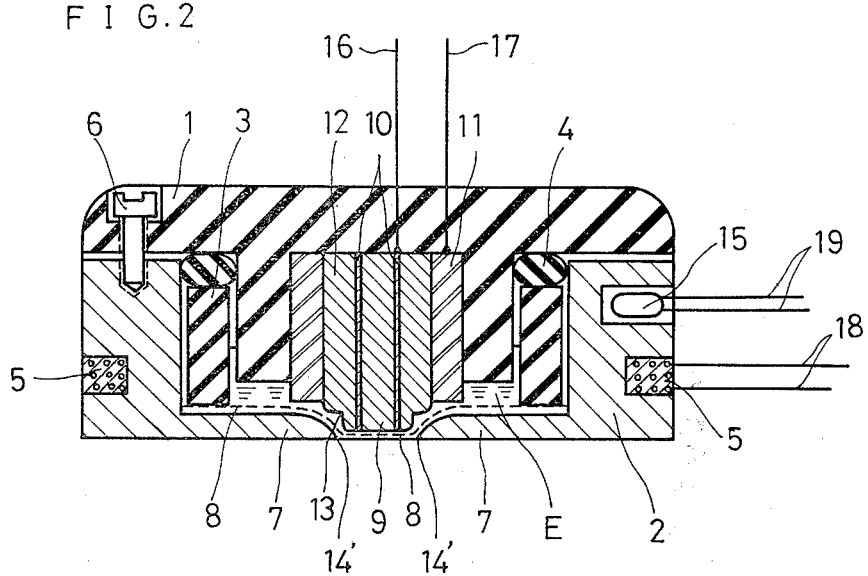
FIG. 2 is a sectional elevation view of one embodiment of an improved transcutaneous blood oxygen measuring device in accordance with the present invention.
Figure 3:
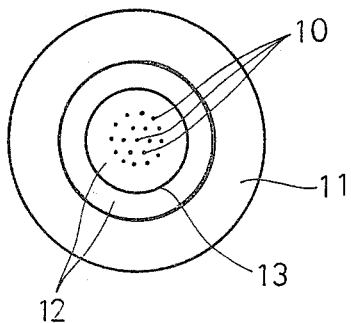
FIG. 3 is a bottom view of the electrode portion of the device shown in FIG. 2.

A preferred embodiment of the present invention is now elucidated in more detail referring to FIG. 2. The improved transcutaneous blood oxygen measuring device shown in FIG. 2 includes a covering member or lid-shaped electrode part 1, a receptacle-shaped heating part 2 for receiving the electrode part 1 and heating the surrounding skin, and a membrane part 3 adapted to retain an oxygen-permeable membrane 8 at its lower end disposed in a space formed between the electrode part 1 and the heating part 2. A sealing ring 4, for example a synthetic rubber ring, is disposed between the top face of the membrane part 3 and the lower face of the lid part of the electrode part 1. A heater 5 is embedded in an annular hollow encircling a ring-shaped metal block portion of the heating part 2, the heater 5 being connected to lead wires 18. Connecting bolts 6 (only one bolt is illustrated) connect the electrode 1 and the heating part 2, with the membrane part 3 and the sealing ring 4 inbetween. The heating part 2 is made of a material having good heat conductivity with a peripheral ring-shaped groove having a heater 5 embedded therein and for heating the surrounding skin a centrally extended plate-like heating part 7 having a relatively small round opening 14' at the center. Also included is a temperature detecting element 15, such as thermistor, embedded in a hollow recess to provide a temperature detection signal through lead wires 19 connected to a known control circuit for controlling the current supplied to the heater 5. The edge of the opening 14' has a tapered shoulder portion wherein the edge of the opening 14' slopes down to the lower face of the heating part 7. When a Clark-type construction is utilized, the electrode part 1 has a thin tube-shaped cathode 10 made of a noble metal, such as platinum or gold, a thick tube-shaped anode 11 made of silver coaxially disposed to surround the cathode 10, and an insulator 12, such as glass, plastics or the like, filled in the spaces between the anode 11 and the cathode 10. Lead wires 16 and 17 are provided to connect the cathode 10 and anode 11, respectively, to a conventional electronic circuit. Alternatively, the cathode may be a bundle of fine wires or needles disposed uniformly in a predetermined area, for example a circular area which is coaxial with the anode 11, as shown in FIG. 3. As the membrane, there may be used an oxygen permeable and hydrophobic plastic film such as polyvinylidenchloride, polytetrafluoroethylene, polypropylene and polyester.

FIG. 3 is a bottom view of the end face of cathode 10, together with an anode 11 and surrounding insulator 12. The anode 11 and the insulator 12 are similar to those of the embodiment of the invention shown in FIG. 2. The cathode 10 consists of a bundle or grouping of fine wires or needles of noble metal disposed generally uniformally in a circular region which is coaxial to the ring-shaped anode 11. Preferably the noble metal of the cathode 10 is platinum or gold, and the bundle of fine wires or needles of the noble metal is embedded in the center of the circular region of the insulator 12 and are uniformly disposed in a circular area which is coaxial to the anode in the region on the end face.

The present invention characterized in that the end face, that is the lower face, of the electrode part 1 has a central protruding portion 9 and an offset or stepped shoulder 13. This means that the lower end face of the insulator 12 facing the membrane 8 is shaped to have a protruding portion 9 at its central part, so that the lower end face of the cathode 10 is carried by the protruding portion 9. On the other hand, the relatively small round opening 14' provides an opening that is slightly larger in size than that of the protruding portion 9. In this arrangement the protruding portion 9 is covered by the electrolyte layer E and the membrane 8 is pushed forward to substantially completely fill the opening. The lower end face of the protruding portion 9 is disposed in such a position that the lower face of the membrane 8 at the part of the protruding portion 9 is slightly offset from the plane of the lower face of the skin heating part 7. The membrane 8 has a predetermined tension that is set when the membrane part 3 is positioned between the electrode part 1 and the heating part 2, since the membrane 8 is placed in position by the protruding portion 9 in cooperation with the sloped edge at the opening 14' of the skin heating part 7.

According to the construction of the present invention, only the small protruding portion 9 of the electrode part 1 is presented to the skin through the narrowed opening 14'. Since the opening at 14' is relatively small the skin surface in the area of the opening can be uniformly heated thus minimizing or substantially completely eliminating any temperature difference between the skin exposed to the membrane through the small opening 14' and the surrounding skin in direct contact with the heating part 7. Moreover, since the area of the membrane 8 which contacts the skin surface is limited to such a small area as defined by the protruding portion 9 of the electrode, excessive pressing against the membrane 8 by the skin becomes less possible, and accordingly, there is substantially no problem that the electrolyte E is squeezed out by an excessive pressing of the membrane. Therefore, the accuracy and stability of the measurement are greatly improved.

What is claimed is:

1. An electrode assembly for the transcutaneous measurement of partial oxygen pressure in arterial blood including in combination;

an electrode portion having a cathode electrode surrounded by an anode electrode and an insulating means between and supporting said anode electrode and said cathode electrode, each of said cathode electrode and said anode electrode having end portions, said insulating means having a first cylindrical end portion and a second cylindrical end portion extending from said first cylindrical end portion to a second and extended position, said second cylindrical end portion being coaxial with said first cylindrical end portion and having a diameter less than said first cylindrical end portion so as to form a step therebetween, said cathode end portion extending at least to said second position;

heating means, connected to said electrode portion, having a face adapted to contact skin for heating skin in contact therewith, said face having an opening for presenting said second cylindrical end portion of said insulating means and with said end portion of said cathode electrode therein; and an oxygen permeable membrane disposed between said face of said heating means and the end portions of said electrodes, the membrane covering said end portions of each of said electrodes and defining a space adapted to retain a liquid electrolyte between the end portions of each of said electrodes and said membrane;

wherein said end portion of said cathode electrode is disposed and extends beyond the plane of the end portion of said anode electrode towards said opening, said end portion of said cathode electrode is positioned concentrically with the axis of said opening such that a surface of said membrane away from said electrode portion, in cooperation with the end portion of said cathode electrode, is slightly offset from the plane of said heating face, and further wherein the opening in said heating means has rounded shoulders adjacent the extending portion of said cathode electrode, the rounded shoulders and cathode end portion positioned in proximity to each other and providing a predetermined tension on the membrane therebetween, said cathode end portion contained in said second cylindrical end portion extending into said opening to effect said offsetting and said tensioning.

2. An electrode assembly for the transcutaneous measurement of partial oxygen pressure in arterial blood comprising the following three parts which are disassemblably assembled to construct the electrode assembly:

(1) an electrode part having a silver anode electrode which has a ring-shaped working surface, a platinum or gold cathode electrode which has a working surface inside said anode electrode and an electrode holder which is made of thermally and electrically insulating material and holds said anode and cathode electrodes in an insulated relation from each other, said electrode holder having a first cylindrical portion and a second cylindrical portion extending from said first portion to a second and extended position said second portion being coaxial with said first cylindrical portion having a diameter less than said first cylindrical portion so as to form a step therebetween, said cathode working surface extending at least to said second position;

(2) a disposable membrane holder part having an oxygen-permeable hydrophobic electrode membrane thereon and a cylindrical tubular shape membrane holder of plastic material which fixedly holds the periphery of said electrode membrane on one of its annular end faces with a predetermined tension; and (3) a skin heating part having an electric heater, a temperature detecting element and a heat conducting metal block to which said heater and said temperature detecting element are heat-conductingly connected, said heat conducting metal block having a thinner disk-shaped inner portion extending unitarily inwards from the bottom portion of a thicker peripheral portion and said inner portion having a through hole of larger size than said cathode working surface to expose therethrough said cathode working surface to subject's skin via said membrane while defining a substantially uniform electrolyte receiving space between said membrane and said anode working surface and said cathode working surface, said hole having rounded sides tapering divergently from said working surface of said cathode electrode, one side of both said peripheral portion and said inner portion of said heat conducting block forming one substantially flat surface to be applied on the subject's skin, the area of said substantially flat surface being larger than the area of said through hole, and another side of said disk-shaped inner portion opposite said one side, forming a receiving space having a receiving face on which said membrane holder part and said electrode part are disposed;

in assembled state, said heat conducting block embracing in its receiving space said membrane holder part, said membrane holder part adapted to receive a liquid electrolyte and substantially embracing therein the anode and the cathode of said electrode part in such a manner that said electrode membrane covers closely said working surfaces of said anode and cathode electrodes via an electrolyte layer;

said working surface of said cathode electrode contained in said second cylindrical portion extending into said hole to effect slight offsetting of the membrane from the plane of said flat surface and a predetermined tensioning of said membrane.

3. A transcutaneous blood oxygen measuring device in accodance with claim 2 or 1 wherein said cathode is a bundle of fine wires of a noble metal disposed uniformly in a circular area which is coaxial to the anode.

4. A transcutaneous blood oxygen measuring device in accordance with claim 2 or 1 wherein said cathode is a thin tube of noble metal disposed coaxially to the anode.

5. A transcutaneous blood oxygen measuring device in accordance with claim 1 wherein said cathode is made of a material selected from the group consisting of platinum and gold and said anode is silver.

6. A transcutaneous blood oxygen measuring device in accordance with claim 2 or 1 wherein said membrane is an oxygen permeable hydrophobic plastic film selected from the group consisting of polyvinlidenchloride, polytetrafluoroethylene, polypropylene and polyester.

7. An electrode assembly for the transcutaneous measurement of partial oxygen pressure in arterial blood comprising the following three parts which are disassemblably assembled to construct the electrode assembly:

an electrode part having an anode which has a ring-shaped working surface, a cathode which has a working surface inside of and extending beyond said anode working surface, and an electrode holder which is made of thermally and electrically insulating material and holds said anode and cathode in an insulated relation from each other, said electrode holder having a first cylindrical portion and a second cylindrical portion extending from said first portion to a second and extended position, said second portion being coaxial with said first cylindrical portion and having a diameter less than said first cylindrical portion so as to form a step therebetween, said cathode working surface extending at least to said second position;

a disposable membrane holder part having an oxygen permeable hydrophobic electrode membrane thereon and a cylindrical tubular shape membrane holder of plastic material which fixedly holds the periphery of said electrode membrane on one of its annular end faces with a predetermined tension, and a skin heating part having an electric heater, a temperature detecting element and a heat conducting metal block to which said heater and said temperature detecting element are heat-conductingly connected, said heat conducting metal block having a thinner disk-shaped inner portion extending unitarily inwards from the bottom portion of a thicker peripheral portion and said inner portion having a through hole of larger size than said cathode working surface to expose therethrough said cathode working surface to subject's skin via said membrane while defining a substantially uniform electrolyte receiving space between said membrane and said cathode working surface and said anode working surface, said hole having rounded sides tapering divergently from said working surface of said cathode, one side of both said peripheral portion and said inner portion of said heat conducting block forming one substantially flat surface to be applied on the subject's skin, the area of said substantially flat surface being larger than the area of said through hole, and another side of said disk-shaped inner portion opposite said side, forming a receiving space having a receiving face on which said membrane holder part and said electrode part are disposed;

in assembled state, said heat conducting block embracing in its receiving space said membrane holder part, said membrane holder part adapted to receive a liquid electrolyte and substantially embracing therein the anode and the cathode of said electrode part in such a manner that said electrode membrane covers closely said working surface of each of said anode and cathode via an electrolyte layer;

said working surface of said cathode contained in said second cylindrical portion extending into said hole to effect slight offsetting of the membrane from the plane of said flat surface and a predetermined tensioning of said membrane.

8. A polarographic electrode assembly in accordance with claim 7 wherein said working surface of the cathode protrudes from a plane on which said periphery of said electrode membrane lies together with said rounded sides of said hole tapered divergently from said cathode, thereby in an assembled state said electrode membane being set with a predetermined tension.

9. A transcutaneous blood oxygen measuring electrode assembly for the transcutaneous measurement of partial oxygen pressure in arterial blood, said device comprising:

an electrode portion having a platinum or gold cathode coaxially surrounded by a silver anode and an insulating means between and supporting said anode and said cathode, said insulating means having a first cylindrical portion and a second cylindrical portion extending from said first portion to a second and extended position, said second portion being coaxial with said first cylindrical portion and having a diameter less than said first cylindrical portion so as to form a step therebetween, an end portion of said cathode extending at least to said second position;

heating means, connected to said electrode portion, having a lower face adapted to contact skin for heating skin in contact therewith, said face having an opening for presenting said end portion of said cathode contained therein, said opening having rounded shoulders adjacent the end portion of the cathode; and an oxygen permeable membrane disposed between said face of said heating means and the end portions of said electrodes, the membrane covering the end portions of each of said electrodes and defining a space adapted to retain a liquid electrolyte between the end portions of each of said electrodes and said membrane, the rounded shoulders of the opening and the end portion of said cathode adapted to provide a predetermined tension on the membrane therebetween, wherein said end portion of said cathode extends beyond the plane of said end portion of said anode to an area closely spaced from said opening, the extended portion of said cathode positioned concentrically with the axis of said opening such that a surface of said membrane away from said electrode portion, in cooperation with the extended cathode portion, is slightly offset from the plane of the lower face of said heating means, said end portion of said cathode contained in said second cylindrical portion extending into said opening to effect said tensioning and said offsetting of said membrane.

* * * * *